(12) United States Patent
Zuberi et al.

(10) Patent No.: US 8,853,679 B2
(45) Date of Patent: Oct. 7, 2014

(54) ORGANIC SEMICONDUCTORS

(75) Inventors: Sheena Zuberi, Harrow (GB); Tania Zuberi, Harrow (GB)

(73) Assignee: Cambridge Display Technology Limited, Cambridgeshire (GB)

( * ) Notice: Subject to any disclaimer, the term of this patent is extended or adjusted under 35 U.S.C. 154(b) by 133 days.

(21) Appl. No.: 13/387,020

(22) PCT Filed: Aug. 5, 2010

(86) PCT No.: PCT/GB2010/001485
§ 371 (c)(1),
(2), (4) Date: Apr. 3, 2012

(87) PCT Pub. No.: WO2012/017184
PCT Pub. Date: Feb. 9, 2012

(65) Prior Publication Data
US 2012/0184089 A1    Jul. 19, 2012

(30) Foreign Application Priority Data

Aug. 5, 2009 (GB) .................................. 0913628.4

(51) Int. Cl.
*H01L 29/12* (2006.01)
(52) U.S. Cl.
USPC ............. 257/40; 548/517; 548/518; 548/527; 549/59; 549/60; 438/99
(58) Field of Classification Search
USPC ............. 257/40, E51.028, E51.029; 548/517, 548/518, 527; 549/59, 60; 438/99
See application file for complete search history.

(56) References Cited

U.S. PATENT DOCUMENTS 5,454,880 A * 10/1995 Sariciftci et al. .............. 136/263
6,528,815 B1 * 3/2003 Brown et al. ................... 257/40
(Continued)

FOREIGN PATENT DOCUMENTS

EP    1 700 860 A1    9/2006
EP    2 248 818 A1    11/2010
(Continued)

OTHER PUBLICATIONS

Bunnagel et al., "Thiophene-Phenylene/naphthalene-Based Step-Ladder Copolymers," *Journal of Polymer Science A: Polymer Chemistry*, 46(22):7342-7353 (2008).
(Continued)

*Primary Examiner* — George Fourson, III
(74) *Attorney, Agent, or Firm* — Marshall, Gerstein & Borun LLP

(57) ABSTRACT

A semiconducting compound comprising the structure:

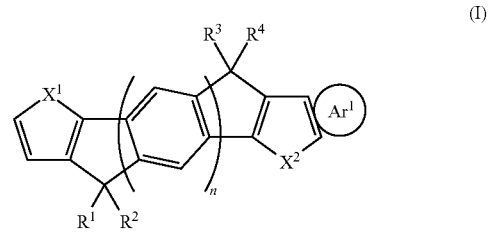

(I)

where R1 to R4 independently comprise, but are not limited to, optionally substituted straight, branched or cyclic alkyl chains having 2 to 20 (e.g. 2 to 12) carbon atoms, alkoxy, amino, amido, silyl, alkyl, alkenyl, aryl or hetero aryl; where X1 and X2 independently comprise S, O, NR5 or SiR6R7 where R8 to R7 independently comprise C1 to C5 branched, straight or cyclic alkyl chains; and where Ar1 comprises a heterocyclic ring, and where n is an integer between 1 and 4.

24 Claims, 3 Drawing Sheets

(56) References Cited

U.S. PATENT DOCUMENTS

| | | | |
|---|---|---|---|
| 2007/0235722 A1* | 10/2007 | Li et al. | 257/40 |
| 2009/0090906 A1 | 4/2009 | Chuman | |
| 2010/0001263 A1* | 1/2010 | Noguchi et al. | 257/40 |
| 2011/0266528 A1* | 11/2011 | Langer et al. | 257/40 |
| 2013/0207047 A1* | 8/2013 | Suda et al. | 252/500 |

FOREIGN PATENT DOCUMENTS

| | | |
|---|---|---|
| JP | 2007-088222 A | 4/2007 |
| JP | 2007-119392 A | 5/2007 |
| JP | 2007-299980 A | 11/2007 |
| WO | WO-00/53656 A1 | 9/2000 |
| WO | WO-2007/068618 A1 | 6/2007 |
| WO | WO-2007/116660 A1 | 10/2007 |

OTHER PUBLICATIONS

Mouri et al., "Ladder Distyrylbenzenes with Silicon and Chalcogen Bridges: Synthesis, Structures, and Properties," *Organic Letters*, 9(1):93-96 (2007).

Tsai et al., "A New Ambipolar Blue Emitter for NTSC Standard Blue Organic Light-Emitting Device," *Organic Electronics*, 10(1):158-162 (2009).

Wong et al., "Synthesis and Structures of Novel Heteroarene-Fused Coplanar π-Conjugated Chromophores," *Organic Letters*, 8(22):5033-5036 (2006).

Xu et al., "Ladder Oligo(p-phenylenevinylene)s with Silicon and Carbon Bridges," *Journal of the American Chemical Society*, 127(6):1638-1639 (2005).

Yamada et al., "Structural Modification of Silicon-Bridged Ladder Stilbene Oligomers and Distyrylbenzenes," *Macromolecular Chemistry and Physics*, 210(11):904-916 (2009).

Yamaguchi et al., "Synthesis, Structures, and Photophysical Properties of Silicon and Carbon-Bridged Ladder Oligo(p-phenylenevinylene)s and Related Pi-Electron System," *Journal of Organometallic Chemistry*, 690:5365-5377 (2005).

Yamamoto, "Electrically Conducting and Thermally Stable π-Conjugated Poly(Arylene)s Prepared by Organometallic Processes," *Prog. Polym. Sci.*, 17:1153-1205 (1993).

International Preliminary Report on Patentability for Application No. PCT/GB2010/001485, dated Feb. 7, 2012.

International Search Report and Written Opinion for Application No. PCT/GB2010/001485, dated Dec. 27, 2011.

Search Report for Application No. GB0913628.4, dated Dec. 22, 2009.

\* cited by examiner

ORGANIC SEMICONDUCTORS

BACKGROUND OF THE INVENTION

1. Field of the Invention

The present invention relates generally to organic semiconductors and in particular to organic semiconductors for forming part of a thin film transistor.

2. Related Technology

Transistors can be divided into two main types: bipolar junction transistors and field-effect transistors. Both types share a common structure comprising three electrodes with a semiconductive material disposed there between in a channel region. The three electrodes of a bipolar junction transistor are known as the emitter, collector and base, whereas in a field-effect transistor the three electrodes are known as the source, drain and gate. Bipolar junction transistors may be described as current-operated devices as the current between the emitter and collector is controlled by the current flowing between the base and emitter. In contrast, field-effect transistors may be described as voltage-operated devices as the current flowing between source and drain is controlled by the voltage between the gate and the source.

Transistors can also be classified as p-type and n-type according to whether they comprise semiconductive material which conducts positive charge carriers (holes) or negative charge carriers (electrons) respectively. The semiconductive material may be selected according to its ability to accept, conduct, and donate charge. The ability of the semiconductive material to accept, conduct and donate holes or electrons can be enhanced by doping the material.

For example, a p-type transistor device can be formed by selecting a semiconductive material which is efficient at accepting, conducting, and donating holes, and selecting a material for the source and drain electrodes which is efficient at injecting and accepting holes from the semiconductive material. Good energy-level matching of the Fermi-level in the electrodes with the HOMO level of the semiconductive material can enhance hole injection and acceptance. In contrast, an n-type transistor device can be formed by selecting a semiconductive material which is efficient at accepting, conducting, and donating electrons, and selecting a material for the source and drain electrodes which is efficient at injecting electrons into, and accepting electrons from, the semiconductive material. Good energy-level matching of the Fermi-level in the electrodes with the LUMO level of the semiconductive material can enhance electron injection and acceptance.

Transistors can be formed by depositing the components in thin films to form a thin film transistor (TFT). When an organic material is used as the semiconductive material in such a device, it is known as an organic thin film transistor (OTFT).

OTFTs may be manufactured by low cost, low temperature methods such as solution processing. Moreover, OTFTs are compatible with flexible plastic substrates, offering the prospect of large-scale manufacture of OTFTs on flexible substrates in a roll-to-roll process.

With reference to FIG. 2, the general architecture of a bottom-gate organic thin film transistor (OTFT) comprises a gate electrode 12 deposited on a substrate 10. An insulating layer 11 of dielectric material is deposited over the gate electrode 12 and source and drain electrodes 13, 14 are deposited over the insulating layer 11 of dielectric material. The source and drain electrodes 13, 14 are spaced apart to define a channel region therebetween located over the gate electrode 12. An organic semiconductor (OSC) material 15 is deposited in the channel region for connecting the source and drain electrodes 13, 14. The OSC material 15 may extend at least partially over the source and drain electrodes 13, 14.

Alternatively, it is known to provide a gate electrode at the top of an organic thin film transistor to form a so-called top-gate organic thin film transistor. In such an architecture, source and drain electrodes are deposited on a substrate and spaced apart to define a channel region there between. A layer of an organic semiconductor material is deposited in the channel region to connect the source and drain electrodes and may extend at least partially over the source and drain electrodes. An insulating layer of dielectric material is deposited over the organic semiconductor material and may also extend at least partially over the source and drain electrodes. A gate electrode is deposited over the insulating layer and located over the channel region.

An organic thin film transistor can be fabricated on a rigid or flexible substrate. Rigid substrates may be selected from glass or silicon and flexible substrates may comprise thin glass or plastics such as poly(ethylene-terephthalate) (PET), poly(ethylene-naphthalate) (PEN), polycarbonate and polyimide.

The organic semiconductive material may be made solution processable through the use of a suitable solvent. Exemplary solvents include mono- or poly-alkylbenzenes such as toluene and xylene; tetralin; and chloroform. Preferred solution deposition techniques include spin coating and ink jet printing. Other solution deposition techniques include dip-coating, roll printing and screen printing.

The length of the channel defined between the source and drain electrodes may be up to 500 microns, but preferably the length is less than 200 microns, more preferably less than 100 microns, most preferably less than 20 microns.

The gate electrode can be selected from a wide range of conducting materials for example a metal (e.g. gold) or metal compound (e.g. indium tin oxide). Alternatively, conductive polymers may be deposited as the gate electrode. Such conductive polymers may be deposited from solution using, for example, spin coating or ink jet printing techniques and other solution deposition techniques discussed above.

The insulating layer comprises a dielectric material selected from insulating materials having a high resistivity. The dielectric constant, k, of the dielectric is typically around 2-3 although materials with a high value of k are desirable because the capacitance that is achievable for an OTFT is directly proportional to k, and the drain current ID is directly proportional to the capacitance. Thus, in order to achieve high drain currents with low operational voltages, OTFTs with thin dielectric layers in the channel region are preferred.

The dielectric material may be organic or inorganic. Preferred inorganic materials include $SiO_2$, $SiN_x$ and spin-on-glass (SOG). Preferred organic materials are generally polymers and include insulating polymers such as poly vinylalcohol (PVA), polyvinylpyrrolidine (PVP), acrylates such as polymethylmethacrylate (PMMA), fluorinated polymers and benzocyclobutanes (BCBs) available from Dow Corning. The insulating layer may be formed from a blend of materials or comprise a multi-layered structure.

The dielectric material may be deposited by thermal evaporation, vacuum processing or lamination techniques as are known in the art. Alternatively, the dielectric material may be deposited from solution using, for example, spin coating or ink jet printing techniques and other solution deposition techniques discussed above.

If the dielectric material is deposited from solution onto the organic semiconductor, it should not result in dissolution of the organic semiconductor. Likewise, the dielectric material should not be dissolved if the organic semiconductor is deposited onto it from solution. Techniques to avoid such dissolution include: use of orthogonal solvents for example use of a solvent for deposition of the uppermost layer that does not dissolve the underlying layer; and cross linking of the underlying layer.

The thickness of the insulating layer is preferably less than 2 micrometers, more preferably less than 500 nm.

Organic semiconductors are a class of organic molecules having extensively conjugated pi systems allowing for the movement of electrons.

Preferred methods for preparation of these molecules are Suzuki reactions (coupling or polymerization reactions) as described in, for example, WO 2000/53656 and Yamamoto polymerization as described in, for example, T. Yamamoto, "Electrically Conducting And Thermally Stable pi-Conjugated Poly(arylene)s Prepared by Organometallic Processes", Progress in Polymer Science 1993, 17, 1153-1205. These techniques both operate via a "metal insertion" wherein the metal atom of a metal complex catalyst is inserted between an aryl group and a leaving group of a monomer. In the case of Yamamoto polymerization, a nickel complex catalyst is used; in the case of Suzuki reaction, a palladium complex catalyst is used.

For example, in the synthesis of a linear polymer by Yamamoto polymerization, a monomer having two reactive halogen groups is used. Similarly, according to the method of Suzuki reaction, at least one reactive group is a boron derivative group such as a boronic acid or boronic ester and the other reactive group is a halogen. Preferred halogens are chlorine, bromine and iodine, most preferably bromine.

Alternatively, stannyl groups may be used as reactive groups in polymerization or coupling reactions (Stille reactions).

The performance of organic semiconductors is typically assessed by measurement of its "charge mobility" (cm$^2$ V$^{-1}$ s$^{-1}$), which may relate to either the mobility of holes or electrons. This measurement relates to the drift velocity of charge carriers to an applied electric field across a material.

Organic semiconductors having relatively high mobilities tend to be those which comprise compounds having a rigid planar structure with extensive conjugation which allows for efficient and effective pi-pi stacking in the solid state.

WO 2007/068618 describes a variety of organic semiconductors, each comprising an array of fused aromatic rings having a central benzene ring substituted with acetylene groups.

JP 2007/088222 and WO 2007/116660 describe the use of benzodithiophenes and its derivatives in small molecule, oligomeric and polymeric form, as organic semiconductors.

Scherf et al. in Journal of Polymer Science A: Polymer Chemistry 46 (22) 7342 to 7353 describe polymers having the structure:

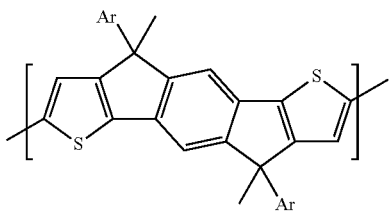

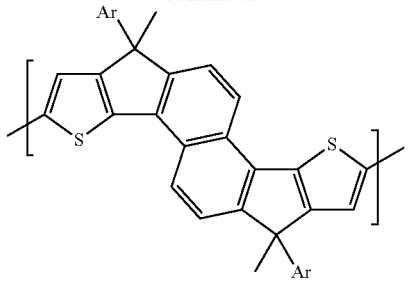

However, the increased level of conjugation required to allow compounds to form such a pi-pi stack may also result in a decrease in band gap and stability of the semiconductor, leading to poor performance and a short lifetime. Moreover, these compounds may be highly insoluble due to the size of molecule required to achieve extended conjugation, which poses particular problems in synthesis and renders their use in efficient transistor production methods, such as ink-jet printing, difficult.

SUMMARY OF THE INVENTION

The present invention seeks to provide an organic semiconductor having high mobility, good solubility and good ambient stability.

In a first aspect, the present invention provides a semiconducting compound as specified in claims 1 to 11. The compound preferably comprises the structure:

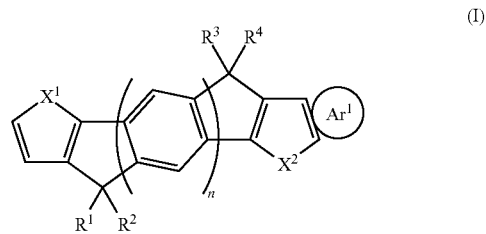

where $R^1$ to $R^4$ independently comprise, but are not limited to, optionally substituted straight, branched or cyclic alkyl chains having between 2 and 20 carbon atoms (preferably 2 to 12 carbon atoms, or 2 to 6 carbon atoms), alkoxy, amino, amido, silyl, alkyl, alkenyl, aryl or hetero aryl;

where $X^1$ and $X^2$ independently comprise S, O, NR$^5$ or SiR$^6$R$^7$ where R$^8$ to R$^7$ independently comprise C$_1$ to C$_5$ branched, straight or cyclic alkyl chains;

where Ar$^1$ comprises a heterocyclic aromatic ring, and where n is an integer between 1 and 4.

While solubilizing groups can be placed anywhere on the structure, the inventors have found that the preferable positioning of solubilizing groups at the "bridge head" positions on five membered rings adjacent the central ring or rings provides a greater solubilizing effect than when positioned at the periphery of the molecule.

Accordingly, shorter and/or smaller solubilizing groups may be used at the bridge head position. These shorter and/or smaller solubilizing groups are less able to interfere with Π-Π stacking, thereby potentially providing improved mobility in addition to improved solution processability.

Moreover, the improved solubility afforded by the positioning of the solubilizing groups allows the planar conjugated structure of the semiconducting species to be further extended while the species remains soluble.

Preferably, the semiconducting compound comprises the structure:

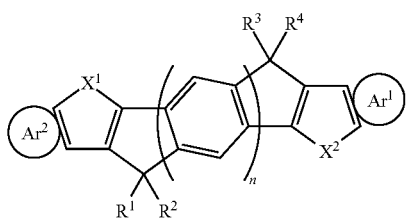

(II)

where $Ar^2$ is a homocyclic or heterocyclic aromatic ring. Where $Ar^2$ is a heterocyclic aromatic ring, it preferably comprises at least one heteroatom selected from the group S, O, $NR^5$ or $SiR^6R^7$.

Preferably, the compound comprises one or more further aromatic groups fused in series to $Ar^1$ and/or, if present, $Ar^2$. One, some, or all of said further aromatic groups may be, and in some embodiments are, heterocyclic groups containing at least one heteroatom selected from the group S, O, $NR^5$ or $SiR^6R^7$.

Preferably one or both of the terminal aryl or heteroaryl groups of the compound is substituted with one or more substituents T, at least one of which groups comprises a reactive or polymerizable group or optionally substituted straight, branched or cyclic alkyl chains having 1 to 20 (e.g. 1 to 12) carbon atoms, alkoxy, amino, amido, silyl, alkyl, alkenyl, aryl or hetero aryl, the remaining groups, if any, independently comprising hydrogen or optionally substituted straight, branched or cyclic alkyl chains having 1 to 20 (e.g. 1 to 12) carbon atoms, alkoxy, amino, amino, amido, silyl, alkyl, or alkenyl.

The reactive polymer group or groups preferably independently comprise such moieties as halogens, boronic acids, diboronic acids, esters of boronic and diboronic acids, alkylene groups or stannyl groups.

The terminal aryl groups represent aryl groups fused to just one other aryl or heroaryl group, for example, group $Ar^1$ and the group containing heteroatom $X^1$ in structure I and groups $Ar^1$ and $Ar^2$ in structure II.

Preferably the compound comprises a structure selected from the group:

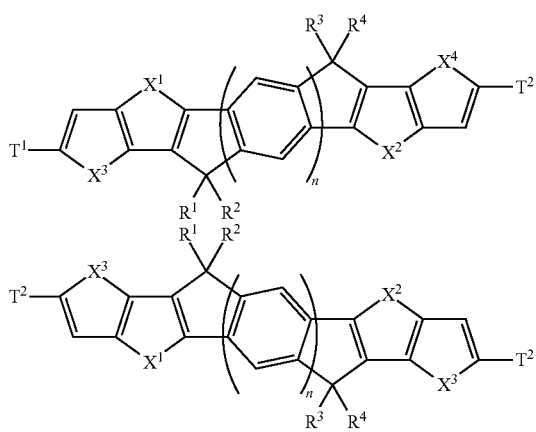

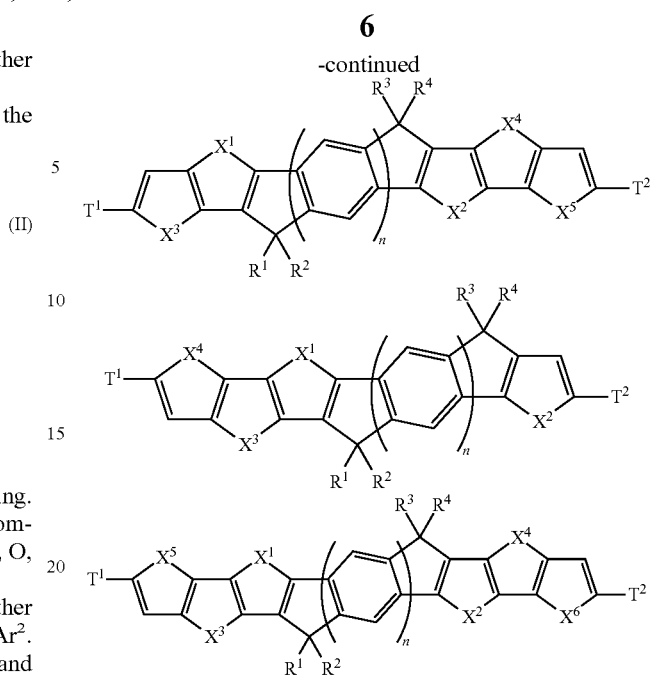

Where $X^3$ to $X^6$ may independently comprise S, O, $NR^5$ or $SiR^6R^7$, and where if any of $X^3$ to $X^6$ is part of a terminal aryl group, $X^3$ to $X^6$, if present, may comprise $C_2H_2$.

Alternatively, the compound may comprise the structure:

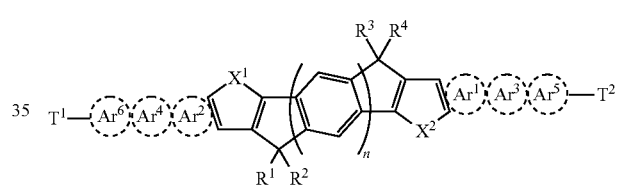

where one or more of the optional aryl groups $Ar^1$ to $Ar^6$ independently comprises a heterocycle including at least one heteroatom selected from the groups: S, O, $NR^5$ or $SiR^6R^7$.

Preferably one or both of the terminal aryl groups comprise homocyclic rings.

In another aspect, the invention provides an electronic device comprising a semiconducting portion comprising a compound described herein.

In another aspect, the invention provides a solution for applying to the surface of a substrate to form a semiconducting portion on the substrate, the solution comprising a compound as described herein.

In a further aspect, the invention provides a method of manufacturing an electronic device comprising applying a solution as described herein onto a substrate.

DETAILED DESCRIPTION

Figure 1:
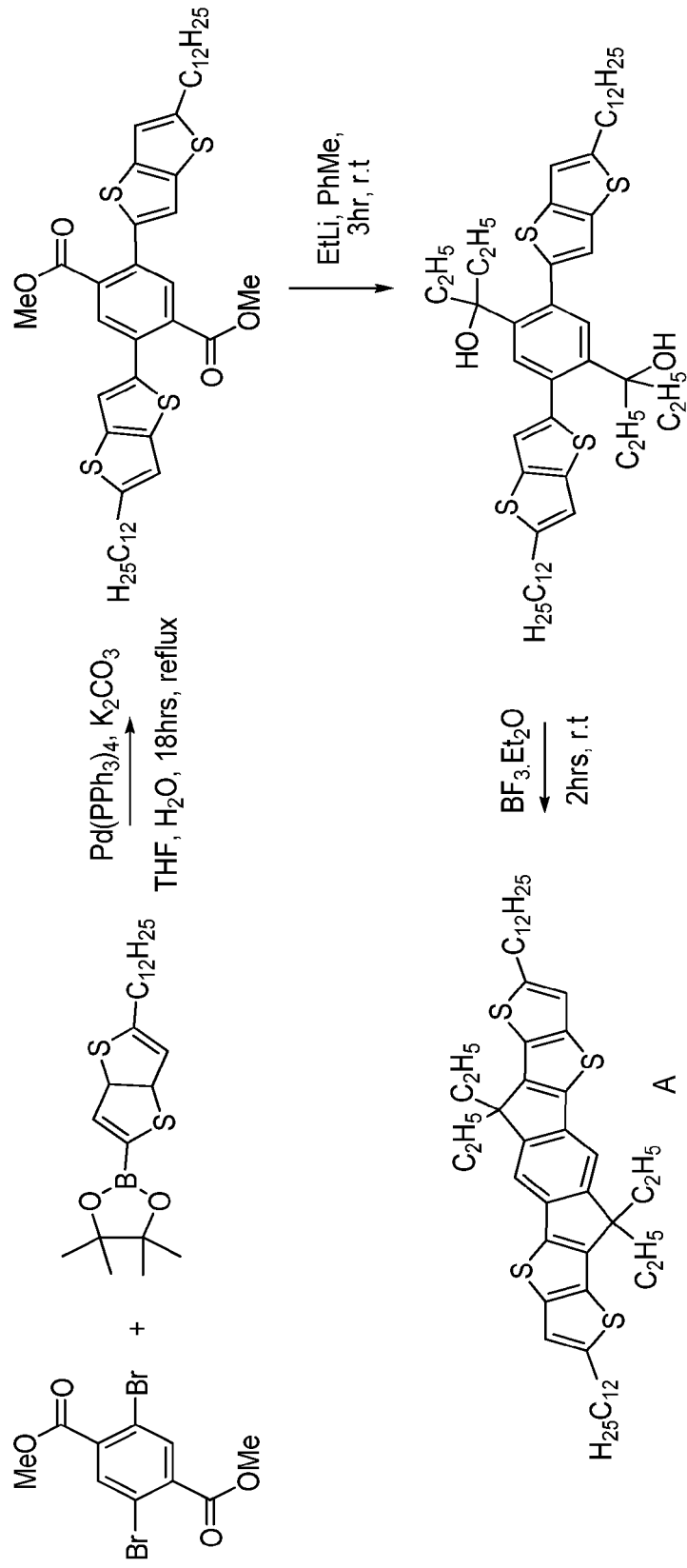
FIG. 1 shows a synthesis of a compound according to the invention.

Throughout the following description like reference numerals shall be used to identify like parts.

Organic semiconductors according to the present invention may be manufactured by means of a Suzuki-type cross-coupling reaction of a pinacol boronate of a thienothiophene with a diethyl-2,5-dibromoterephthalate in the presence of Pd(PPh$_3$)$_4$ and K$_2$CO$_3$ to give a diketo compound. Further reaction with methyl lithium followed by a BF3.Et2O-mediated cyclization affords the compounds of the invention as shown in FIG. 1.

Other compounds which may be manufactured by this method are shown below:

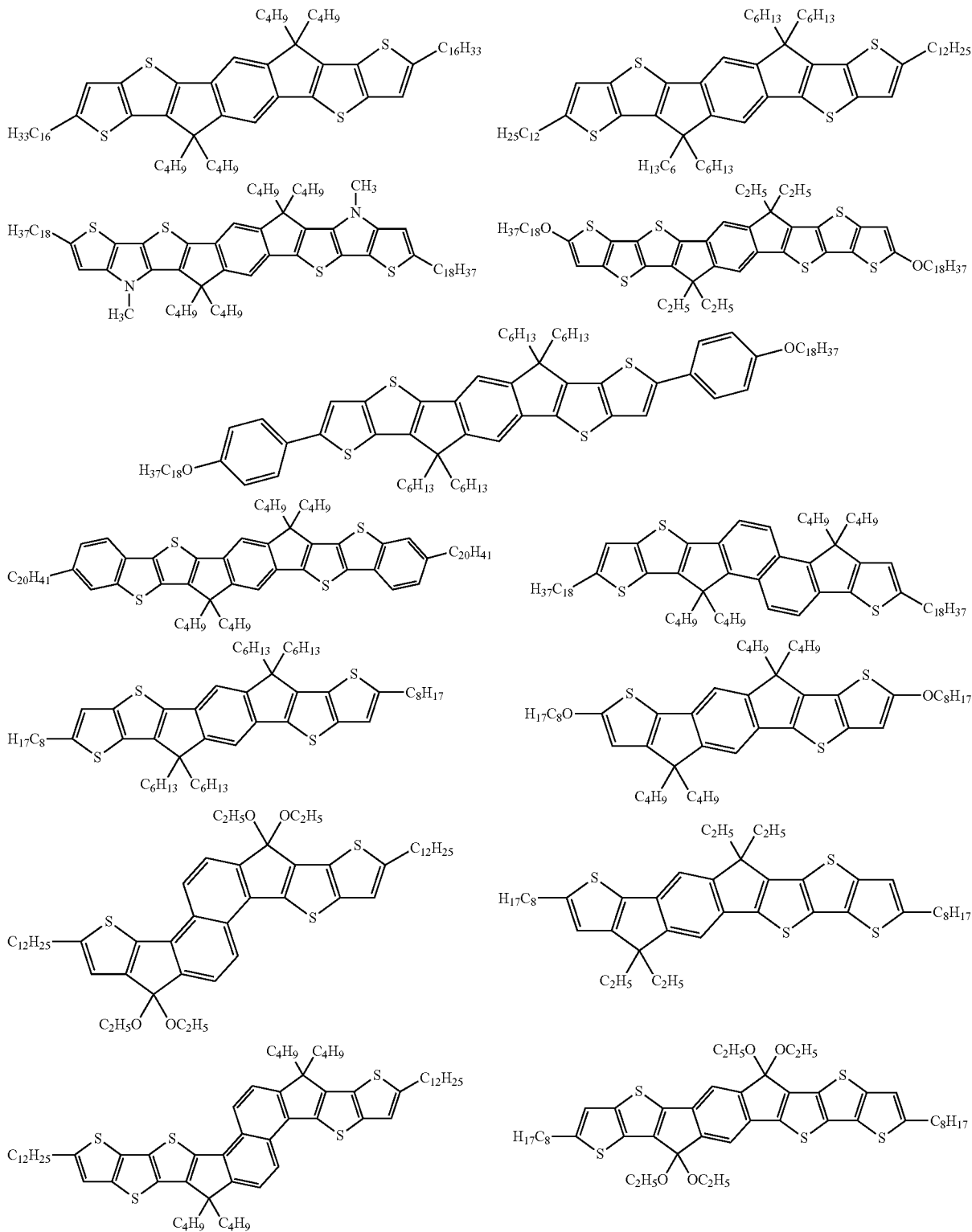

-continued
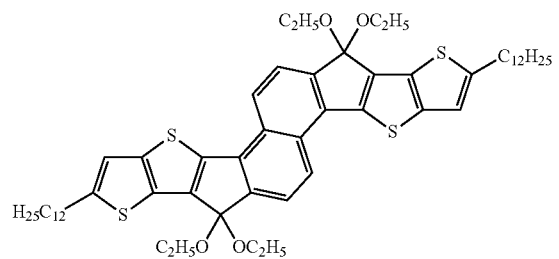
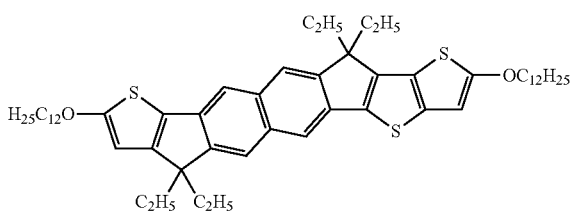
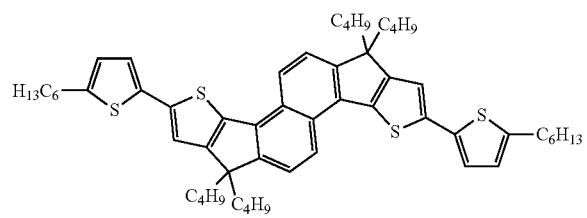
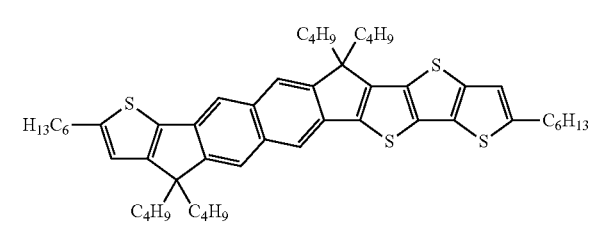
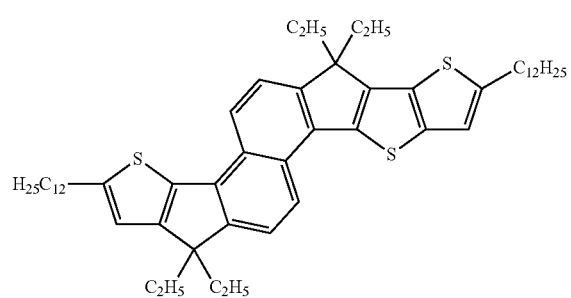
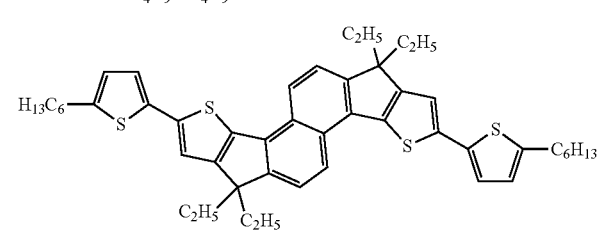
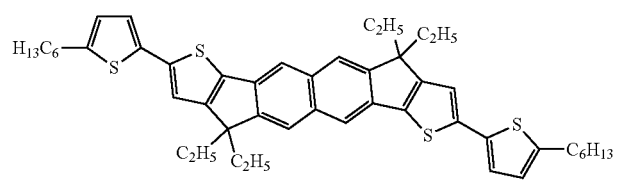
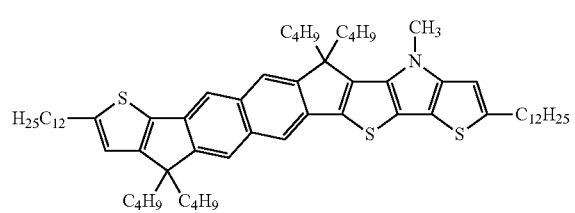
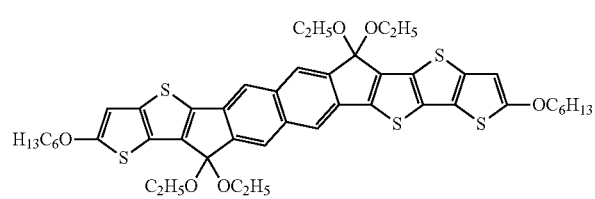
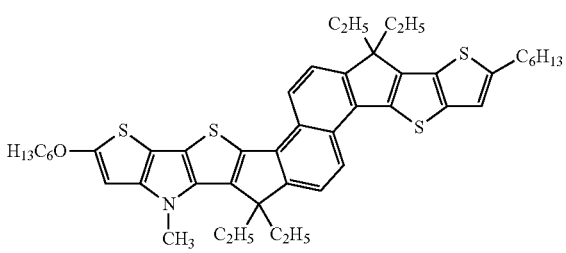
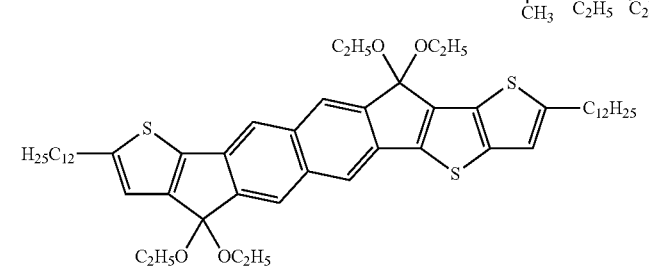
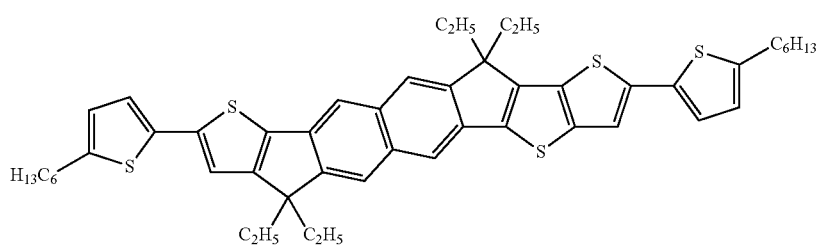

-continued
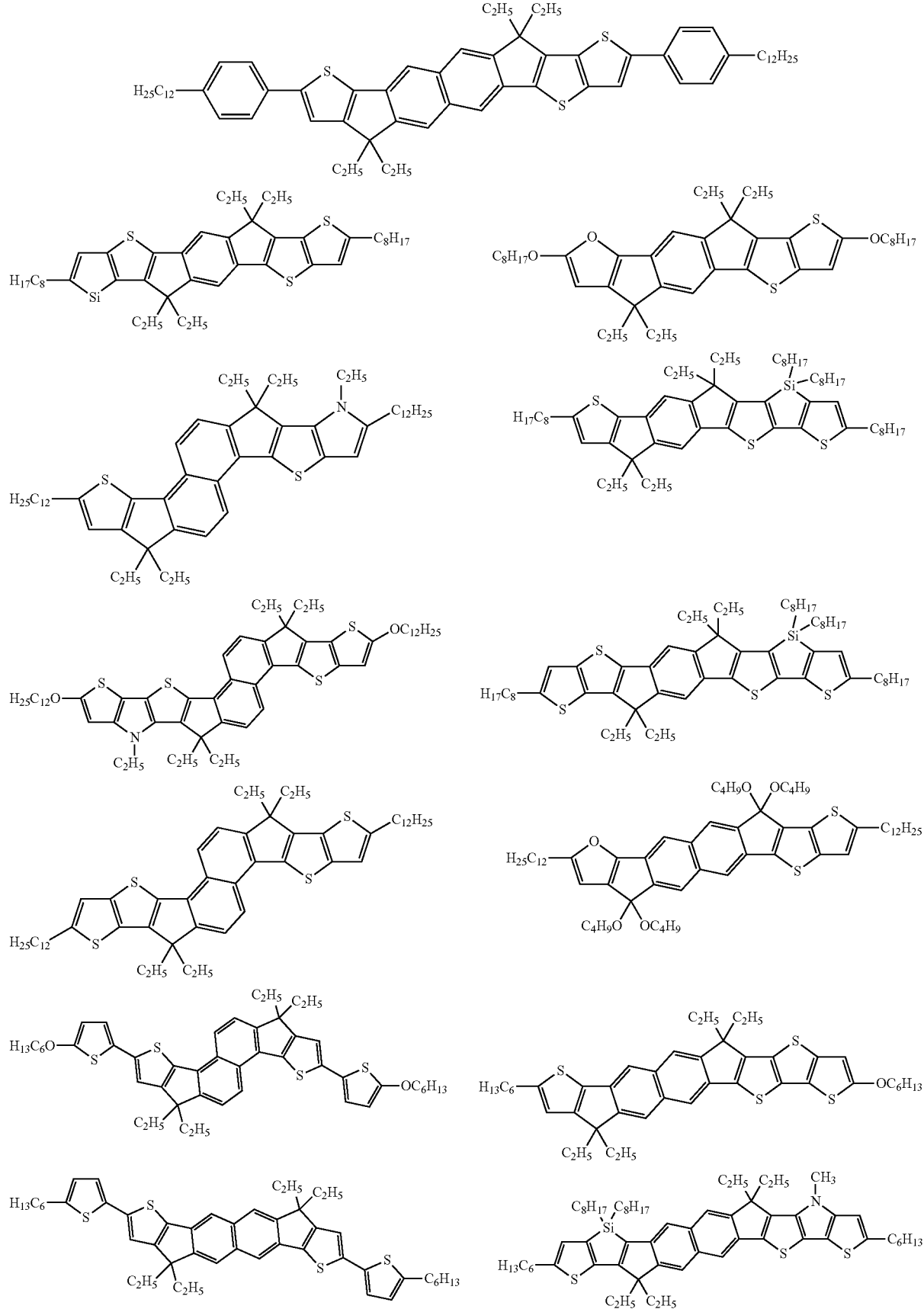

-continued

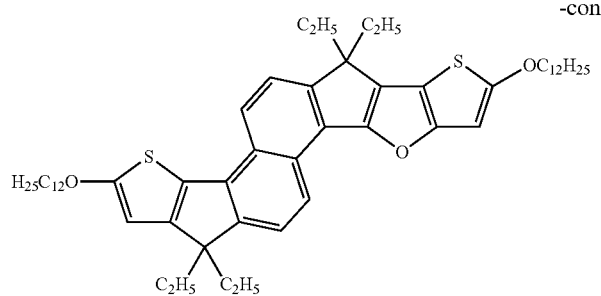
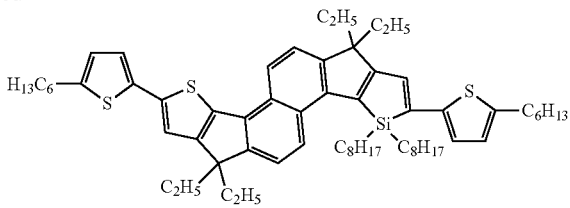
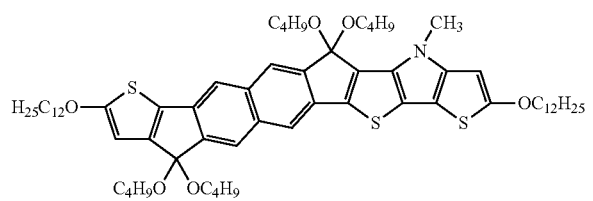
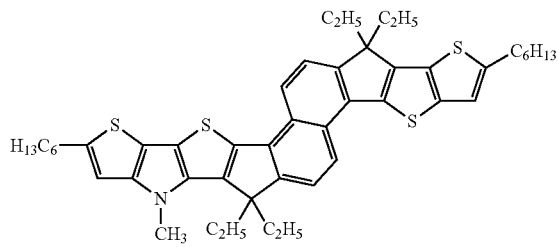
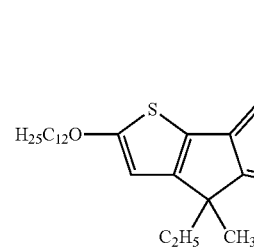
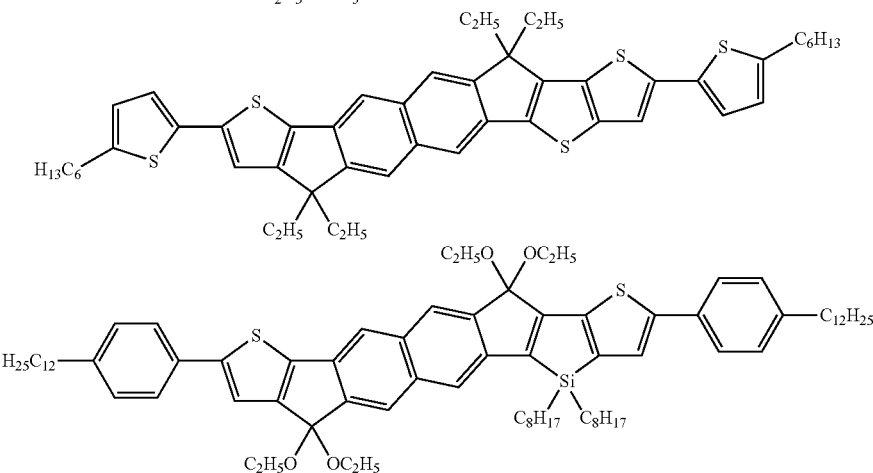

Figure 2:
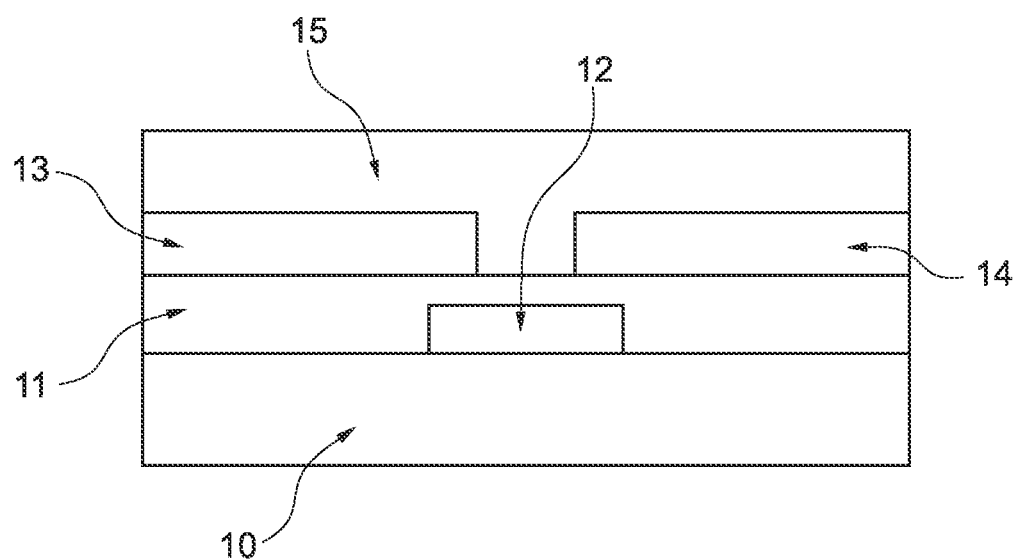
FIG. 2 is a schematic diagram of a general architecture of a bottom-gate organic thin film transistor according to the prior art.

The resulting compounds are easily soluble and may thus be applied by ink-jet printing or other suitable solution deposition technique onto a substrate to provide the semiconducting layer 15 in a thin film transistor such as is shown in FIG. 2.

An application of such an organic thin film transistor (OTFT) may be to drive pixels in an optical device, preferably an organic optical device. Examples of such optical devices include photoresponsive devices, in particular photodetectors, and light-emissive devices, in particular organic light emitting devices. OTFTs are particularly suited for use with active matrix organic light emitting devices, e.g. for use in display applications.

Figure 3:
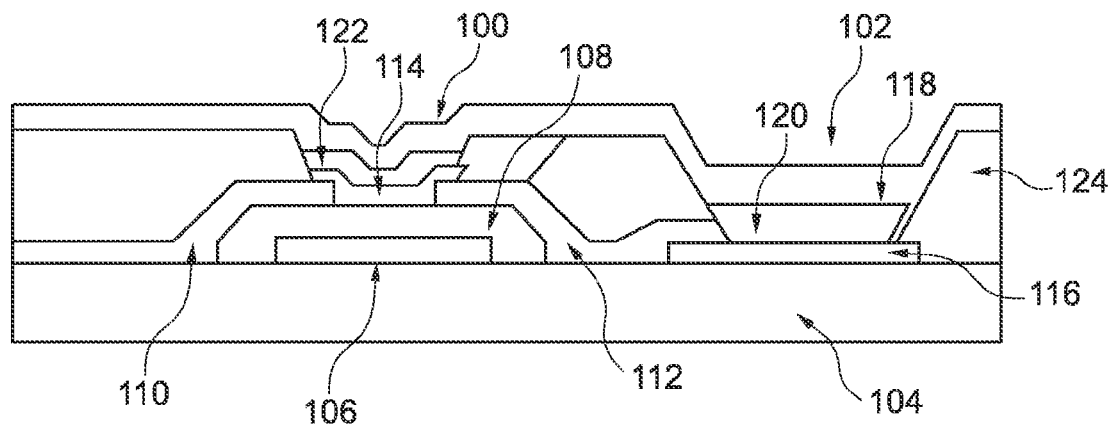
FIG. 3 is a schematic diagram of a pixel comprising an organic thin film transistor and an adjacent organic light emitting device fabricated on a common substrate according to an embodiment of the present invention; and, FIG. 4 is a schematic diagram of an organic thin film transistor fabricated in a stacked relationship to an organic light emitting device according to an embodiment of the present invention.

FIG. 3 shows a pixel comprising an organic thin film transistor 100 and an adjacent organic light emitting device (OLED) 102 fabricated on a common substrate 104. The OTFT 100 comprises gate electrode 106, dielectric layer 108, source and drain electrodes 110 and 112 respectively, and OSC layer 114. The OLED 102 comprises anode 116, cathode 118 and an electroluminescent layer 120 provided between the anode 116 and cathode 118. Further layers may be located between the anode 116 and cathode 118, such as charge transporting, charge injecting or charge blocking layers. In the embodiment of FIG. 3, the layer of cathode material 118 extends across both the OTFT 100 and the OLED 102, and an insulating layer 122 is provided to electrically isolate the cathode layer 118 from the OSC layer 122. The active areas of the OTFT 100 and the OLED 102 are defined by a common bank material formed by depositing a layer of photoresist 124 on substrate 104 and patterning it to define OTFT 100 and OLED 102 areas on the substrate.

In FIG. 3, the drain electrode 112 is directly connected to the anode 116 of the organic light emitting device 102 for switching the organic light emitting device 102 between emitting and non-emitting states.

Figure 4:
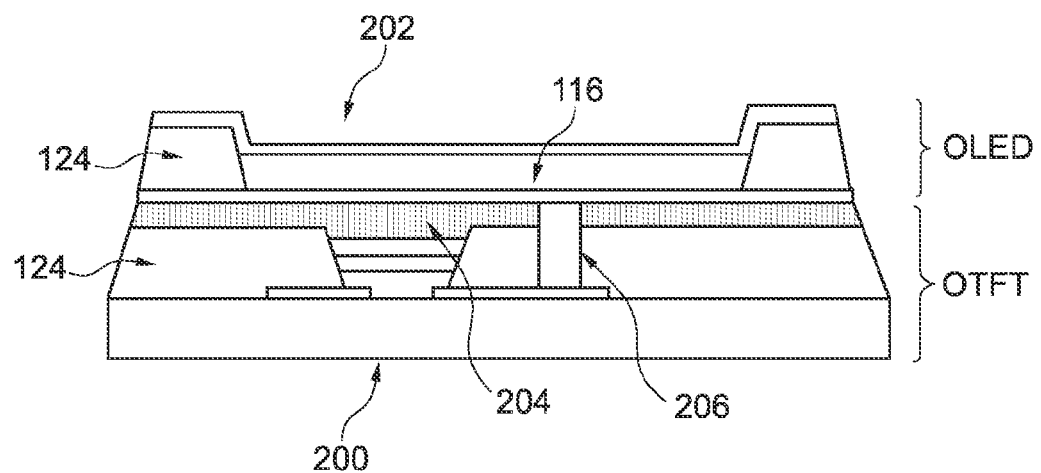

In an alternative arrangement illustrated in FIG. 4, an organic thin film transistor 200 may be fabricated in a stacked relationship to an organic light emitting device 202. In such an embodiment, the organic thin film transistor 202 is built up as described above in either a top or bottom gate configuration. As with the embodiment of FIG. 3, the active areas of the OTFT 200 and OLED 202 are defined by a patterned layer of photoresist 124, however in this stacked arrangement, there are two separate bank layers 124—one for the OLED 202 and one for the OTFT 200. A planarization layer 204 (also known as a passivation layer) is deposited over the OTFT 200. Exemplary passivation layers 204 include BCBs and parylenes. The organic light emitting device 202 is fabricated over the passivation layer 204 and the anode 116 of the organic light emitting device 202 is electrically connected to the drain electrode 112 of the OTFT 200 by a conductive via 206 passing through passivation layer 204 and bank layer 124.

It will be appreciated that pixel circuits comprising an OTFT and an optically active area (e.g. light emitting or light sensing area) may comprise further elements. In particular, the OLED pixel circuits of FIGS. 3 and 4 will typically comprise least one further transistor in addition to the driving transistor shown, and at least one capacitor. It will be appreciated that the organic light emitting devices described herein may be top or bottom-emitting devices. That is, the devices may emit light through either the anode or cathode side of the device. In a transparent device, both the anode and cathode are transparent. It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminum.

Transparent cathodes are particularly advantageous for active matrix devices because emission through a transparent anode in such devices may be at least partially blocked by OTFT drive circuitry located underneath the emissive pixels as can be seen from the embodiment illustrated in FIG. 4.

Thicknesses of the gate electrode, source and drain electrodes may be in the region of 5-200 nm, although typically 50 nm as measured by Atomic Force Microscopy (AFM), for example.

Other layers may be included in the device architecture. For example a self assembled monolayer (SAM) may be provided on the gate, source or drain electrodes, and/or one may be provided on the substrate, insulating layer and organic semiconductor material to promote crystallinity, reduce contact resistance, repair surface characteristics and promote adhesion where required. In particular, the dielectric surface in the channel region may be provided with a monolayer comprising a binding region and an organic region to improve device performance, e.g. by improving the organic semiconductor's morphology (in particular polymer alignment and crystallinity) and covering charge traps, in particular for a high k dielectric surface. Exemplary materials for such a monolayer include chloro- or alkoxy-silanes with long alkyl chains, e.g. octadecyltrichlorosilane.

No doubt many other effective alternatives will occur to the skilled person. It will be understood that the invention is not limited to the described embodiments and encompasses modifications apparent to those skilled in the art lying within the scope of the claims appended hereto.

The invention claimed is:

1. A semiconducting compound comprising the structure:

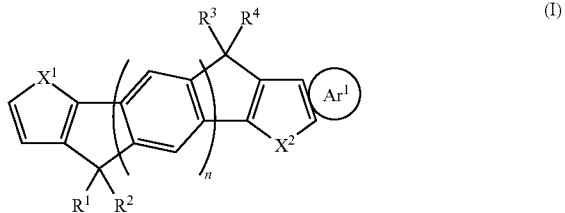

(I)

where $R^1$ to $R^4$ independently comprise optionally substituted straight, branched, or cyclic alkyl chains having between 2 and 20 carbon atoms, alkoxy, amino, amido, silyl, alkyl, alkenyl, aryl, or heteroaryl;

where $X^1$ and $X^2$ independently comprise S, O, $NR^5$, or $SiR^6R^7$ where $R^5$ to $R^7$ independently comprise $C_1$ to $C_5$ branched, straight, or cyclic alkyl chains; and, where $Ar^1$ is a heterocyclic aromatic ring, where n is an integer between 1 and 4.

2. A semiconducting compound according to claim 1 comprising the structure:

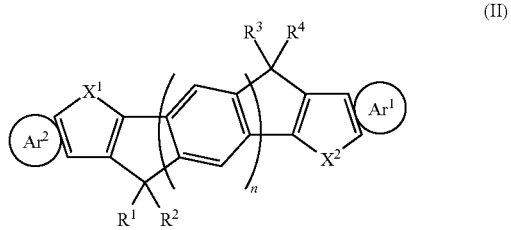

(II)

where $Ar^2$ is a homo-cyclic or heterocyclic aromatic ring.

3. A semiconducting compound according to claim 2 where $Ar^2$ is a heterocyclic aromatic ring.

4. A semiconducting compound according to claim 1, where the compound comprises one or more further aromatic groups fused in series to $Ar^1$.

5. A semiconducting compound according to claim 4 wherein one, some, or all of said further aromatic groups comprises heterocyclic groups.

6. A semiconducting compound according to claim 1 comprising two terminal aryl groups wherein at least one of the terminal aryl groups is substituted with one or more substituents T, at least one of which substituents T comprises an optionally substituted straight, branched, or cyclic alkyl chain having 1 to 20 carbon atoms, alkoxy, amino, amido, silyl, alkyl, alkenyl, aryl, or heteroaryl, the remaining substituents T independently comprising hydrogen, an optionally substituted straight, branched or cyclic alkyl chain having 1 to 20 carbon atoms, alkoxy, amino, amino, amido, silyl, alkyl, or alkenyl.

7. A semiconducting compound according to claim 6, wherein the compound comprises a structure selected from the group consisting of:

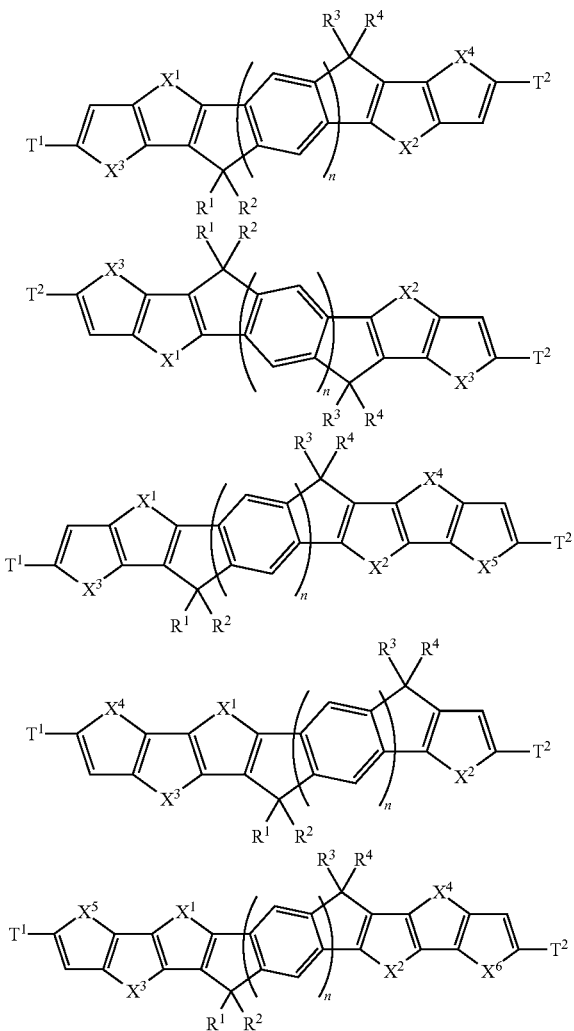

where $X^3$ to $X^6$ independently comprise S, O, $NR^5$, or $SiR^6R^7$, $T^1$ and $T^2$ comprise substituents T, and where any of $X^3$ to $X^6$ is part of a terminal aryl group.

8. A semiconducting compound comprising the structure:

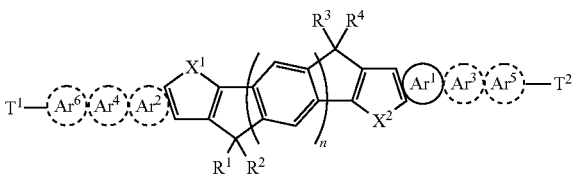

where $R^1$ to $R^4$ independently comprise optionally substituted straight, branched, or cyclic alkyl chains having 1 to 20 carbon atoms, alkoxy, amino, amido, silyl, alkyl, alkenyl, aryl, or heteroaryl;

where $X^1$ and $X^2$ independently comprise S, O, $NR^5$, or $SiR^6R^7$ where $R^5$ to $R^7$ independently comprise $C_1$ to $C_5$ branched, straight, or cyclic alkyl chains;

where $T^1$ and $T^2$ independently comprise optionally substituted straight, branched or cyclic alkyl chains having 1 to 20 carbon atoms, alkoxy, amino, amido, silyl, alkyl, alkenyl, aryl, or heteroaryl; and, where one or more of the optional aryl groups $Ar^2$ to $Ar^6$ independently comprises a heterocycle including at least one heteroatom selected from the groups: S, O, $NR^5$, or $SiR^6R^7$.

9. A semiconducting compound according to claim 8, comprising two terminal aryl groups wherein at least one terminal aryl group comprises a homocyclic ring.

10. A semiconducting compound as claimed in claim 1 in which $R^1$ to $R^4$ are the same or different, and independently comprise optionally substituted straight, branched, or cyclic alkyl chains having between 2 and 12 carbon atoms.

11. A semiconducting compound as claimed in claim 10 in which $R^1$ to $R^4$ are the same or different, and independently comprise optionally substituted straight, branched, or cyclic alkyl chains having between 2 and 6 carbon atoms.

12. An electronic device comprising a semiconducting portion comprising a semiconducting compound according to claim 1.

13. A solution for applying to the surface of a substrate to form a semiconducting portion on the substrate, the solution comprising a semiconducting compound according to claim 1.

14. A method of manufacturing an electronic device comprising applying a solution according to claim 13 to a substrate.

15. A semiconducting compound as claimed in claim 1 where $Ar^1$ is a heterocyclic aromatic ring comprising at least one heteroatom selected from the group S, O, $NR^5$ or $SiR^6R^7$.

16. A semiconducting compound according to claim 3 where $Ar^2$ is a heterocyclic aromatic ring comprising at least one heteroatom selected from the group consisting of S, O, $NR^5$, and $SiR^6R^7$.

17. A semiconducting compound according to claim 2, where the compound comprises one or more further aromatic groups fused in series to at least one of $Ar^1$ and $Ar^2$.

18. A semiconducting compound according to claim 17 wherein at least one of said further aromatic groups comprises a heterocyclic group containing at least one heteroatom selected from the group consisting of S, O, $NR^5$, and $SiR^6R^7$.

19. A semiconducting compound according to claim 7, wherein at least one of $X^4$ to $X^6$ comprises $C_2H_2$.

20. A semiconducting compound as claimed in claim 8 in which $R^1$ to $R^4$ are the same or different, and independently comprise optionally substituted straight, branched, or cyclic alkyl chains having between 2 and 12 carbon atoms.

21. A semiconducting compound as claimed in claim 20 in which $R^1$ to $R^4$ are the same or different, and independently comprise optionally substituted straight, branched, or cyclic alkyl chains having between 2 and 6 carbon atoms.

22. An electronic device comprising a semiconducting portion comprising a semiconducting compound according to claim 8.

23. A solution for applying to the surface of a substrate to form a semiconducting portion on the substrate, the solution comprising a semiconducting compound according to claim 8.

24. A method of manufacturing an electronic device comprising applying a solution according to claim 23 to a substrate.

* * * * *